United States Patent
Rubinstein

Patent Number: 5,433,701
Date of Patent: Jul. 18, 1995

[54] APPARATUS FOR REDUCING OCULAR PRESSURE

[76] Inventor: Mark H. Rubinstein, 3317 Woodview Lake, W. Bloomfield, Mich. 48323

[21] Appl. No.: 361,150

[22] Filed: Dec. 21, 1994

[51] Int. Cl.$^6$ .................................................. A61M 1/00
[52] U.S. Cl. ........................................... 604/8; 604/9; 604/294; 604/28
[58] Field of Search ..................... 604/8–10, 604/30, 31, 294, 265–266, 66–67

[56] References Cited

U.S. PATENT DOCUMENTS

| | | |
|---|---|---|
| 4,037,604 | 7/1977 | Newkirk . |
| 4,402,681 | 9/1983 | Haas et al. . |
| 4,428,746 | 1/1984 | Mendez . |
| 4,521,210 | 6/1985 | Wong . |
| 4,558,698 | 12/1985 | O'Dell . |
| 4,722,724 | 2/1988 | Schocket . |
| 4,729,761 | 3/1988 | White . |
| 4,750,901 | 6/1988 | Molteno . |
| 4,826,478 | 5/1989 | Schocket . |
| 4,886,488 | 12/1989 | White . |
| 4,946,436 | 8/1990 | Smith . |
| 4,968,296 | 11/1990 | Ritch et al. . |
| 5,041,081 | 8/1991 | Odrich . |
| 5,092,837 | 3/1992 | Ritch et al. . |
| 5,127,901 | 7/1992 | Odrich . |
| 5,178,604 | 1/1993 | Baerveldt . |
| 5,346,464 | 9/1994 | Camras . |
| 5,370,607 | 12/1994 | Memmen . |

Primary Examiner—C. Fred Rosenbaum
Assistant Examiner—Perry E. Van Over
Attorney, Agent, or Firm—Gifford, Krass, Groh, Sprinkle, Patmore, Anderson & Citkowski

[57] ABSTRACT

An apparatus for reducing pressure in an anterior chamber of an eye. The apparatus includes an anterior portion configured for implantation through a scleral tunnel such that a leading edge thereof is within the anterior chamber. A plurality of channels are defined through the anterior portion, the channels being open to an external environment of the anterior portion to provide fluid communication between the anterior chamber of the eye and the channels. The apparatus further includes a body portion extending from the anterior portion distal the leading edge of the anterior portion of the apparatus. The body portion is configured for implantation between conjunctival and scleral tissues of the eye. The body portion defines a channel therethrough, the channel being in fluid communication with one or more of the plurality of channels formed through the anterior portion of the apparatus. Occlusion means are disposed in one or more of the channels formed through the anterior portion of the apparatus. Each of the occlusion means has a first position in which flow through the channels formed through the anterior portion is obstructed and a second position in which flow through the channels formed through the anterior portion is not obstructed. The occlusion means is adjustable between the first position and the second position to provide selective control of the flow of aqueous through the apparatus.

16 Claims, 2 Drawing Sheets

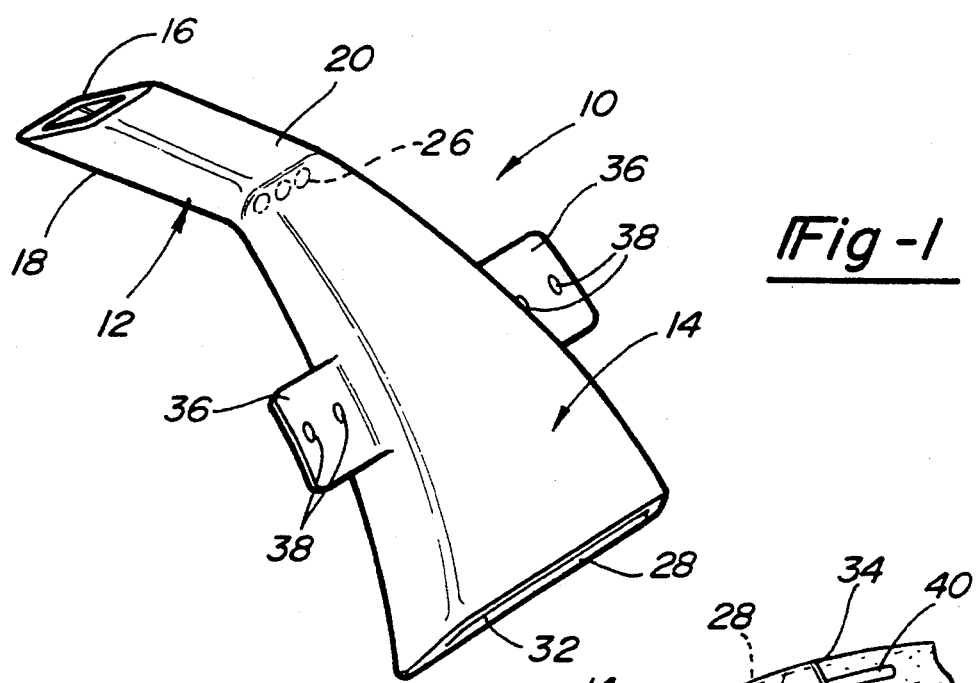
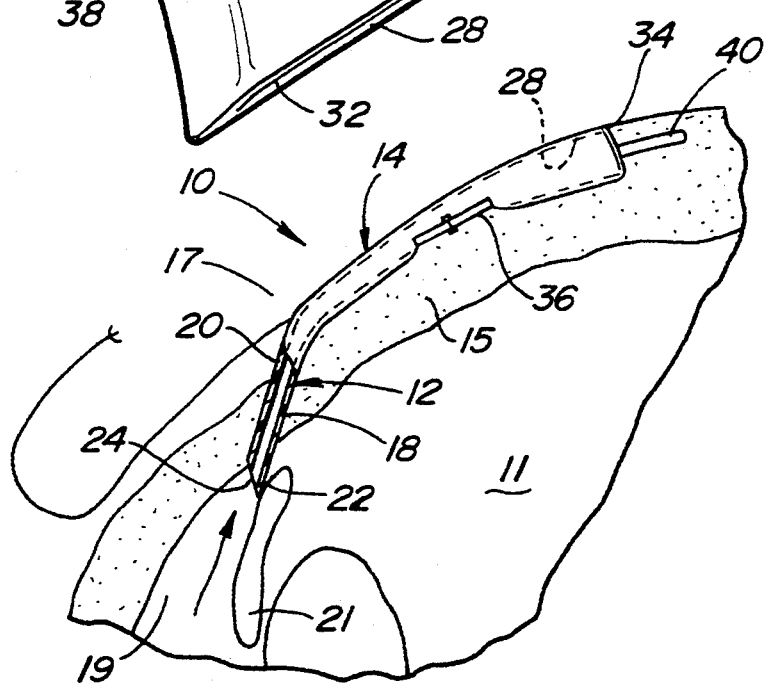
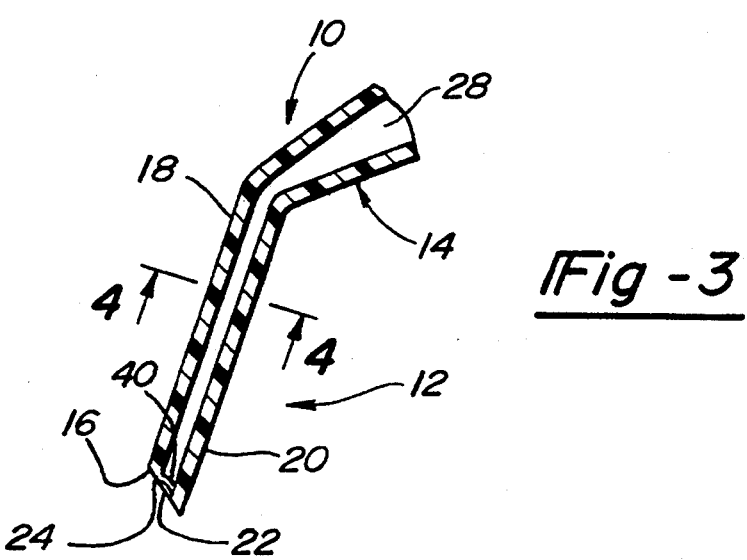

APPARATUS FOR REDUCING OCULAR PRESSURE

BACKGROUND OF THE INVENTION

The present invention relates to an apparatus for reducing intraocular pressure. In particular, the present invention is directed to an apparatus configured for implantation in the eye for the purpose of draining aqueous from the anterior chamber of the eye, thereby reducing intraocular pressure. Glaucoma is a disease marked by an increase in intraocular pressure. The increase in intraocular pressure is principally attributable to a failure of the tissues of the eye to drain aqueous from the anterior chamber of the eye at an adequate rate, although in certain cases an over-production of aqueous by the eye is the cause of the increased pressure. Over time, persistently heightened intraocular pressure will cause permanent damage to ocular tissues, often resulting in blindness. For this reason, it is desirable to maintain the intraocular pressure at It physiologically acceptable level.

Various techniques have been used in an effort to control intraocular pressure. For example, hypotensive agents are commonly prescribed in an effort to reduce the production of aqueous by the eye. Although the use of such hypotensive agents is effective in some cases, this pharmacological approach fails to address the true cause of the increased intraocular pressure, i.e., the failure of the eye to drain aqueous from the anterior chamber. Thus, in many patients it becomes necessary and desirable to facilitate the drainage of aqueous from the anterior chamber of the eye through the use of an implantable drain or shunt.

A variety of devices have been-proposed and used by various ophthalmologists for the purpose of draining aqueous from the anterior chamber of the eye. For example, U.S. Pat. No. 4,457,757 to Molteno discloses a shunt that includes a tube fluidly connected at its first end to a plate. The second end of the tube is configured for insertion into the anterior chamber of the eye, thereby providing a flow path from the anterior chamber to the plate. The plate portion of the Molteno device is configured to lie on the external surface of the eye following implantation of the second end portion of the tube in the anterior chamber. Shunt devices of the type disclosed by Molteno commonly produce an undesirable drop in intraocular pressure, i.e., hypotonicity, immediately following implantation, thereby resulting in damage to the ocular tissues. In addition, such devices provide no ability to control the flow rate of aqueous therethrough. Thus, these implants cannot be adjusted to suit the needs of the particular person into which they are implanted. Accordingly, it is desirable to provide a shunt device that is capable of providing a flow path for the removal of aqueous from the anterior chamber of the eye without causing hypotonicity. In addition, it is desirable to provide a shunt device whose flow resistance can be adjusted so as to accommodate the needs of the particular patient into which it is implanted.

SUMMARY OF THE INVENTION

The apparatus of the present invention includes an anterior portion configured for implantation in the anterior chamber of the eye. The apparatus further includes a body portion extending posteriorly from the anterior portion of the apparatus, the body portion being configured for implantation in the eye. A plurality of channels are formed through the anterior portion of the apparatus such that aqueous from the anterior chamber of the eye can pass through the anterior portion into the body portion of the apparatus when one or more of the plurality of channels is in an open condition. The body portion of the apparatus defines a flow channel therethrough, said flow channel being in fluid communication with at least one of the plurality of channels formed through the anterior portion of the apparatus such that aqueous from the anterior chamber can be directed through the apparatus and into the ocular tissues surrounding the body portion of the apparatus. At least one of the plurality of channels formed through the anterior portion has an occlusion means associated therewith such that the flow of aqueous through at least one of the plurality of channels can be selectively opened subsequent to implantation of the apparatus in the eye to accommodate the particular needs of the patient into which the apparatus is implanted.

In one embodiment of the apparatus of the present invention the occlusion means includes a body of biocompatible material configured such that a portion thereof cast be positioned in at least one of the flow of aqueous channels. The body of biocompatible material is configured such that it can be selectively removed from the channel, thereby providing an unobstructed flow of aqueous through the channel.

The present invention further includes a method for reducing intraocular pressure. The method includes the step of providing an implantable shunt apparatus having a plurality of valved channels formed therethrough. The method further includes the steps of opening the conjunctiva and forming an incision through the scleral tissues in order to create a scleral tunnel providing access to the anterior chamber of the eye. An anterior portion of the implantable shunt apparatus is then inserted into the scleral tunnel such that a leading edge of the anterior portion of the apparatus is positioned within the anterior chamber of the eye. A body portion of the implantable shunt apparatus is then secured to the sclera of the eye and the conjunctiva is closed about the body portion of the implantable shunt apparatus. Following healing of the ocular tissues, one or more of the occlusion channels formed through the apparatus is selectively opened in order to provide the desired amount of flow through the apparatus, thereby reducing intraocular pressure.

BRIEF DESCRIPTION OF THE DRAWINGS

For a more complete understanding of the present invention, reference may be had to the following Detailed Description read in connection with the accompanying drawings in which:

FIG. 1 is an elevational view of an apparatus built in accordance with the present invention;

FIG. 2 is a side view of a preferred embodiment of the invention;

FIG. 3 is a fragmentary view of a portion of a preferred embodiment;

DETAILED DESCRIPTION

Figure 4:
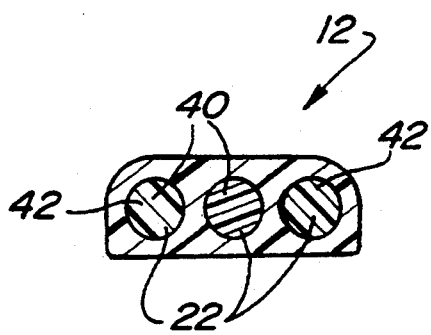
FIG. 4 is an anterior end view of a preferred embodiment built in accordance with the present invention.

An implant for reducing intraocular pressure in accordance with the present invention is generally depicted at 10 in FIG. 1. Implant 10 is preferably constructed of a biocompatible material such as a hydrogel or silicone so that it is not rejected by the body following implantation. Hydrogels and silicone are particularly suited for use in connection with implant 10 in that they are relatively flexible, thereby minimizing the possibility that implant 10 will damage or penetrate surrounding ocular tissues when the eye is touched or moved. Implant 10 includes an anterior portion 12 and a body portion 14. Anterior portion 12 is configured for implantation in the anterior chamber of the eye through a scleral tunnel formed in accordance with the method of the present invention. Body portion 14 preferably is configured for implantation between the sclera and the conjunctiva.

In one embodiment of implant 10, body portion 14 is curved such that it substantially follows the curvature of the eye 11. It will be appreciated that this configuration of body portion 14 will provide greater stability for implant 10 while simultaneously minimizing trauma to surrounding ocular tissues.

Anterior portion 12 can be constructed to be substantially co-planar with body portion 14. However, as best shown in FIGS. 2 and 3, anterior portion 12 is disposed at an angle relative to body portion 14. This configuration permits body portion 14 to lie securely between the sclera 15 and the conjunctiva 17 (FIG. 2) while also ensuring that anterior portion 12 extends appropriately into the anterior chamber 19 of the eye without coming into contact with the iris 21. The precise angle between anterior portion 12 and body portion 14 should be selected based upon several factors, including the position in which the individual physician will place implant 10 and the size and condition of the patient's eye. It will be appreciated that this configuration of anterior portion 12 and body portion 14 will provide greater stability to implant 10 when it is in place in the eye due to the fact that it allows body portion 14 to lie securely on the scleral tissue when implant 10 is implanted.

Anterior portion 12 includes a leading edge 16. Leading edge 16 can have a variety of spatial orientations relative to the remainder of anterior portion 12. However, in the embodiment of the present invention depicted in FIG. 1, leading edge 16 is beveled such that posterior surface 18 of anterior portion 12 is longer than anterior surface 20 of anterior portion 12. This configuration of implant 10 of the present invention minimizes the possibility that the iris will tend to come into contact with leading edge 16 of anterior portion 12, thereby reducing or obviating the need to perform an iridectomy when implanting implant 10. This benefit of the present invention will be described in greater detail below.

As best shown in FIG. 4, a plurality of channels 22 are formed through anterior portion 12. The orientation of channels 22 within anterior portion 12 can be varied without departing from the intended spirit and scope of the present invention. For example, channels 22 can be open through posterior surface 18 or anterior surface 20 of anterior portion 12. However, in the embodiment of implant 10 depicted in FIGS. 1-4, anterior ends 24 of channels 22 are open through leading edge 16 of anterior portion 12 such that there is fluid communication between the external environment of leading edge 16 and channels 22 formed through anterior portion 12. In this embodiment of the present invention, the above-described beveling of, leading edge 16 thus will tend to minimize the possibility that the iris will obstruct the passage of aqueous from the anterior chamber of the eye into channels 22 due to the length of posterior surface 18 of anterior portion 12.

Posterior ends 26 of channels 22 are positioned proximal to body portion 14 of implant 10 relative to anterior ends 24 of channels 22.

As best shown in FIGS. 2 and 3, a channel 28 is formed through body portion 14. Anterior end 30 of channel 28 is in fluid communication with posterior ends 26 of channels 22 such that fluid can flow from channels 22 through channel 28. Posterior end 32 of channel 28 is open through posterior edge 34 of body portion 14, thereby providing fluid communication between the external environment of posterior edge 34 and channel 28.

Posterior edge 34 preferably is constructed such providing a space to avoid scarring of ocular tissues immediately adjacent to implant 10.

The cross-sectional area of channel 28 preferably is at least as large as the dimension of channels 22 such that channel 28 does not restrict the rate of flow through channels 22. Preferably, the dimension of channel 28 is larger than the sum of the dimensions of channels 22, thereby permitting channel 28 to serve as a collection chamber for aqueous drained from the anterior chamber of the eye. In addition, it will be appreciated that the dimension or area of channel 22 is preferably relatively large such that aqueous reaching posterior edge 34 of body portion 14 is exposed to a relatively large surface area of ocular tissue, thereby facilitating absorption of the aqueous and reducing intraocular pressure.

Although the embodiment of the present invention depicted in FIGS. 1 and 2 includes only one channel 28, it will be understood that implant 10 can be modified such that body portion 14 includes a plurality of channels 28 in fluid communication with channels 22.

One or more sidewings fixation elements 36 are mounted on body portion 14 in order to secure implant 10 in the eye. In one embodiment of the present invention, two fixation elements 36 are mounted on body portion 14. Fixation elements 36 can have one or more suture holes 38 formed therethrough such that implant 10 can be sutured into the desired position within the eye. Fixation elements 36 preferably are curved to conform to the shape of the eye. It will be appreciated that the curved shape of the fixation elements 36 will tend to stabilize implant 10 within the eye.

Channels 22 through anterior portion 12 can be of equal or different dimensions. It will be appreciated that the magnitude of aqueous drained through implant 10 will be directly proportional to the total dimension of channels 22 that are providing drainage of aqueous. By varying the dimension of channels 22, it is possible to provide greater flexibility in the total dimension of channels 22, thus allowing the surgeon greater latitude in 10 selecting the amount of drainage to be effected by implant 10.

In the event that channels 22 are of different dimensions, it may be preferable to provide markings on channels 22 to identify the respective sizes of each of channels 22. For example, channels 22 can be color coded to facilitate a determination of the dimension of each of channels 22.

Figure 5:
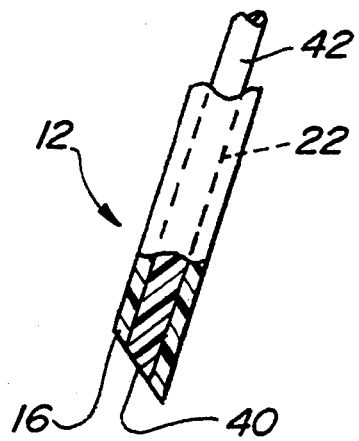
FIG. 5 is a fragmentary view of a portion of a preferred embodiment.

With reference now to FIGS. 4 and 5, occlusion means 40 are provided in at least one and preferably more of channels 22 formed through anterior portion 12. Occlusion means 40 perform two primary functions. First, occlusion means 40 prevent excess flow of aqueous from the anterior chamber immediately following implantation of implant 10, thereby preventing hypotony. That is, occlusion, means 40 are configured such that they obstruct, in whole or in part, the passage of aqueous through channels 22 at the time implant 10 is implanted in the eye. Since, in the preferred embodiment of the invention, occlusion means are provided in each channel 22 there is no immediate change in outflow resistance following implantation. Consequently, excess outflow of fluid from the eye is avoided.

Second, occlusion means 40 are configured such that they can be selectively opened subsequent to implantation of implant 10, thereby allowing the magnitude of flow through implant 10 to be adjusted to the needs of the individual patient into which it is placed. For example, a patient requiring a lesser amount of drainage may have only one of occlusion means 40 opened to permit the passage of aqueous through one of the channels 22 while a patient requiring a greater degree of drainage may have two or more of occlusion means 40 opened to permit drainage through additional channels 22. Furthermore, the individual occlusion means can be simply and individually removed at any time after surgery to increase the outflow in precalculated amounts to compensate for changes in the eye.

In practice, the implant 10 is positioned anteriorly on the globe, i.e., by the limbus, to ease insertion. Furthermore, since the implant is mounted on the globe under the conjunctiva, scarring around the implant is avoided by the elevation of the conjunctiva and drainage into the central cavity is achieved.

In one embodiment of implant 10 of the present invention, occlusion means 40 comprises body or strand 42 of biocompatible material such as a suture. Body 42 is configured such that it can be inserted into channel 22 in order to occlude the flow of aqueous therethrough. Body 42 can be configured to occlude the flow of aqueous completely, or body 42 can be configured to occlude the flow of aqueous only partially, dependent upon the needs of the individual patient as determined by the physician. It will be appreciated that body 42 will serve to prevent the occurrence of hypotony immediately following implantation of implant 10. Body 42 is configured such that it can be selectively removed from channel 22 after implantation of implant 10. For example, body 42 of the first alternative embodiment can be thread-like in shape and dimensioned such that it can be inserted into channel 22 with a portion thereof extending posteriorly from channel 28 (see FIG. 2), thereby facilitating the grasping and removal of body 42 from channel 22. Alternatively, body 42 can be constructed of an ablatable material that can be destroyed by energy delivered from an energy source external of the eye when implant 10 is in place in the eye. For example, laser energy could be used to ablate body 42, thereby opening one or more of channels 22. It also will be appreciated that body 42 be a composite material consisting of layers of materials having different ablation characteristics, thereby permitting the selective destruction of only a portion of body 42 using energy at a preselected level.

Figure 6:
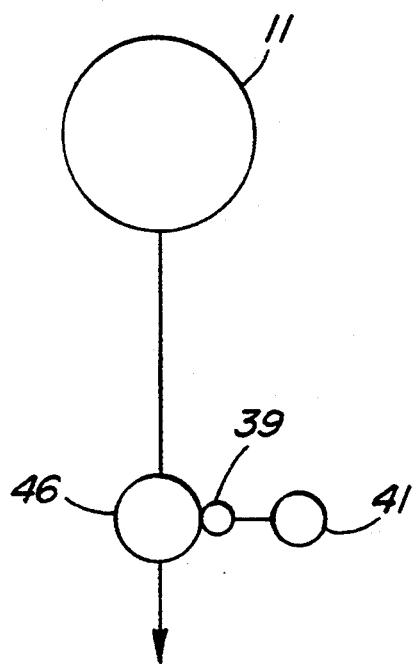
FIG. 6 and FIG. 7 are diagrammatic views illustrating further preferred embodiments of the invention.

In a second alternative embodiment of implant 10 of the present invention depicted diagrammatically in FIG. 6, valve means 41 includes an adjustable valve that can be selectively opened following implantation of implant 10. The valve means 41 can be constructed to operate between a first position in which the adjustable valve occludes flow through channel 22 and a second position in which the adjustable valve does not occlude flow through channel 22. However, it is preferable that valve means 40 be adjustable to provide a larger number of operating positions, thereby allowing the ophthalmologist to adjust the rate of flow of aqueous through implant 10 based upon the needs of the individual patient into which implant 10 is placed. Control of the adjustable valve of this alternative embodiment of the present invention can be effected manually or electronically using known techniques and technologies dependent upon the type of adjustable valve selected.

Alternatively, the valve means 41 is configured such that it physically occludes flow through channel 22 by placing external pressure on the exterior of channels 22, thereby reducing the internal dimension of channels 22. In this third alternative embodiment, channels 22 preferably are formed of a deformable material in order to facilitate the use of valve means 41. Again, it will be appreciated that valve means 41 of this third alternative embodiment can be used to occlude the flow of aqueous through channels 22 either completely or partially dependent upon the needs of the individual patient. Valve means 41 of this alternative embodiment preferably is adjustable such that channels 22 can be selectively opened to varying degrees following implantation of implant 10. Adjustment of valve means 41 in this alternative embodiment can be effected using known manual and electrical techniques.

In a further alternative embodiment of the present invention depicted diagrammatically in FIG. 6, valve means 41 includes a variable outflow modulator 39 capable of selectively increasing or decreasing the degree of outflow resistance through channel 22. The outflow modulator 39 is preferably controlled by a pressure sensor 46 mounted on anterior portion 12 of implant 10 for the purpose of monitoring intraocular pressure within the anterior chamber of the eye. As the intraocular pressure increases, pressure sensor 46 sends a signal to outflow modulator 42 causing a corresponding decrease in the magnitude of outflow resistance imparted by outflow modulator 39. Conversely, when the intraocular pressure decreases below a predetermined level, pressure sensor 46 sends a signal to outflow modulator 42 causing an increase in the magnitude of outflow resistance imparted by outflow modulator 46.

Figure 7:
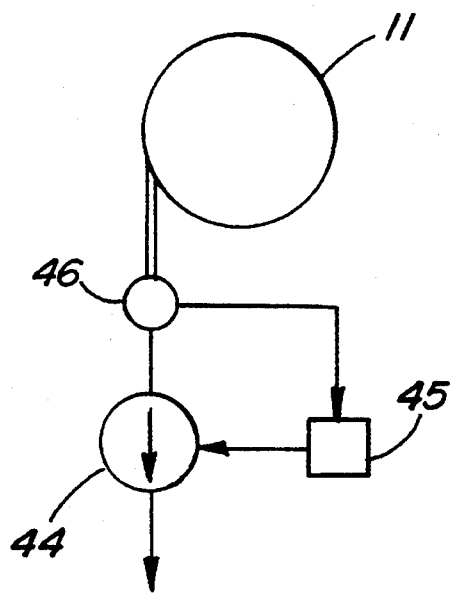

Implant 10 as depicted in FIG. 7 can also include a pump 44 configured to force aqueous through channels 22, 28 in order to effect the removal of aqueous from the anterior chamber of the eye. Pump 44 is preferably adjustable by a rheostat 45 in order to provide selective control over the amount of aqueous withdrawn from the anterior chamber of the eye. The rheostat, in turn, is adjustable by means external to the body, e.g. wave energy, so as to avoid additional surgery. In one embodiment, pump 44 is controlled by a signal generated by pressure sensor 46 mounted on anterior portion 12 of implant 10 for the purpose of monitoring intraocular pressure within the anterior chamber of the eye. When the intraocular pressure exceeds a predetermined level, pressure sensor 46 generates a signal that activates pump 44 at a rate commensurate with the amount that the intraocular pressure exceeds the predetermined level. When the intraocular pressure reaches the desired level, pressure sensor 46 generates a signal that deactivates pump 44. Pressure sensor 46 and pump 44 also can be configured such that pump 44 will effect a reverse flow of aqueous through implant 10 in the event that the intraocular pressure is lower than a preselected level.

Implant 10 can be implanted in the eye using a variety of implantation techniques. The implantation method of the present invention entails the opening of the conjunctiva of the eye to form a limbal flap. Although it is possible to form the conjunctival flap such that it folds away from the limbus, it has been found to be preferable to form a limbal-based conjunctival flap, i.e., a flap that folds toward the limbus. A small incision is then made in order to form a pocket adjacent to the limbus of eye. Next, an incision is made through the sclera into the anterior chamber of the eye, thereby creating a scleral tunnel that enters the anterior chamber anterior to the iris. A glaucoma shunt device such as implant 10 of the present invention can then be inserted into the scleral tunnel such that a leading edge of the implant lies in fluid communication with the anterior chamber of the eye and such that a posterior portion of the implant lies on the sclera of the eye. If desired, the implant can be sutured in place on the sclera of the eye in order to minimize the possibility that the implant will shift positions within the eye following implantation. The conjunctival flap is then closed over the top of the shunt implant. The incisions into the eye are then permitted to heal. After a predetermined healing period, the physician can elect to open one or more of the selectively openable channels using a technique particularly suited to the type of implant used. For example, where a removable body of biocompatible material is disposed in one or more of the channels formed through the implant the biocompatible material can be accessed by a small snip incision through the conjunctiva over the implant. The physician can then selectively remove the body of biocompatible material from one or more of the channels in order to provide the desired degree of drainage of aqueous from the anterior chamber. It will be appreciated that further adjustment of flow rate can be effected by reopening the conjunctiva and removing additional bodies of biocompatible material until all channels formed through the implant have been cleared.

In an alternative embodiment of the method of the present invention, the biocompatible material disposed in the channels formed through the implant is ablatable by energy, e.g., laser energy, delivered from a source external of the eye. In this embodiment, energy is directed to individual channels for the purpose of ablating the body of ablatable, biocompatible material disposed therein, thereby selectively opening individual channels through the device. It will be appreciated that this process can be repeated to open additional channels if needed.

Although the device and method of the present invention have been described herein with reference to certain preferred embodiments, it will be obvious to one of ordinary skill in the art that various modifications can be made without departing from the intended spirit and scope of the present invention.

I claim:

1. An apparatus for reducing pressure in an anterior chamber of an eye, said apparatus comprising:
    an implant having two ends and at least two elongated channels formed between said ends of said implant,
    means for securing said implant to the eye so that one end of said implant is positioned within an anterior chamber of the eye while the other end of said implant is positioned externally of the eye,
    means for selectively occluding said at least two elongated channels, said occluding means being removable from said implant subsequent to securing said implant to the eye.

2. The invention as defined in claim 1 wherein said implant comprises at least two channels extending between said ends of said implant, and said occluding means being provided in each channel, each occluding means being independently removable from its associated channel.

3. The invention as defined in claim 1 wherein said implant comprises at least three channels extending between said ends of said implant, and said occluding means being provided in each channel, each occluding means being independently removable from its associated channel.

4. The invention as defined in claim 1 wherein said implant comprises a body contoured to flatly abut against an outer surface of the sclera of the eye.

5. The invention as defined in claim 4 wherein said body is secured between the conjunctiva and sclera.

6. The invention as defined in claim 4 wherein said securing means comprises at least one flap secured to and extending outwardly from said body.

7. The invention as defined in claim 6 wherein said flap has a suture hole formed through it.

8. The invention as defined in claim 6 and wherein said securing means comprises two flaps secured to and extending outwardly from said body.

9. The invention as defined in claim 1 wherein said occluding means comprises a strand.

10. The invention as defined in claim 1 wherein said occluding means comprises a laser ablatable material.

11. The invention as defined in claim 1 wherein said one end of said implant is positioned anteriorly of an iris of the eye.

12. The invention as defined in claim 11 wherein said one end of said implant comprises a posterior surface and an anterior surface, said posterior surface having a greater longitudinal length than said anterior surface.

13. An apparatus for reducing pressure in an anterior chamber of an eye, said apparatus comprising:
    a pump having an inlet and an outlet,
    means for fluidly connecting said pump inlet to the anterior chamber of the eye,
    means for fluidly connecting said pump outlet to a body cavity,
    means for sensing fluid pressure in the anterior chamber of the eye,
    means responsive to said pressure sensing means for selectively activating said pump to maintain fluid pressure in the anterior chamber within predefined ranges.

14. The invention as defined in claim 13 wherein said activating means comprises a rheostat.

15. The invention as defined in claim 14 and comprising means for adjusting said rheostat externally of the body.

16. A method for reducing pressure in an anterior chamber of an eye comprising the steps of:
    securing an implant to the eye so that one end of the implant is positioned within the anterior chamber of the eye and a second end of the implant is positioned exteriorly of the eye, said implant having at least one fluid passageway extending between said ends of the implant and means for occluding said passageway,
    allowing the eye to substantially heal,
    thereafter removing said occluding means.

* * * * *